(12) United States Patent
Cleary

(10) Patent No.: US 6,935,858 B2
(45) Date of Patent: Aug. 30, 2005

(54) ELASTOMERIC FORCE MODULE FOR ORTHODONTIC TREATMENT

(75) Inventor: James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 94 days.

(21) Appl. No.: 10/299,377

(22) Filed: Nov. 19, 2002

(65) Prior Publication Data
US 2004/0096798 A1 May 20, 2004

(51) Int. Cl.⁷ ................................................ A61C 3/00
(52) U.S. Cl. ........................................................ 433/18
(58) Field of Search ............................. 493/11, 15, 18, 493/19

(56) References Cited

U.S. PATENT DOCUMENTS

| | | | |
|---|---|---|---|
| 3,530,583 A | 9/1970 | Klein et al. | |
| 3,758,947 A | 9/1973 | Kesling | |
| 3,803,715 A | 4/1974 | Wallshein | |
| 3,913,228 A | 10/1975 | Wallshein | |
| 4,038,753 A | 8/1977 | Klein | |
| 4,054,997 A | 10/1977 | Wallshein | |
| 4,330,271 A * | 5/1982 | Anderson | 433/3 |
| 4,412,820 A | 11/1983 | Brummond et al. | |
| 4,565,722 A | 1/1986 | Highgate et al. | |
| 4,946,385 A | 8/1990 | Eckert et al. | |
| 4,950,158 A | 8/1990 | Barngrover et al. | |
| 5,184,954 A * | 2/1993 | Hanson | 433/18 |
| 5,461,133 A | 10/1995 | Hammar et al. | |
| 5,829,974 A * | 11/1998 | Brosius | 433/15 |
| 5,964,588 A | 10/1999 | Cleary | |
| 6,120,289 A | 9/2000 | Cleary et al. | |
| 6,254,383 B1 * | 7/2001 | White | 433/18 |
| 6,280,186 B1 | 8/2001 | Logan | |
| 6,488,498 B1 | 12/2002 | Mariani, Jr. | |
| 2001/0049081 A1 | 12/2001 | Krupp | |

OTHER PUBLICATIONS

3M Unitek Product Catalog 2001–2002, pp. 7-4-7-11.
Pending U.S. Appl. No. 10/078,970, filed Feb. 18, 2002 (56512US002).

* cited by examiner

Primary Examiner—Cary E. O'Connor
(74) Attorney, Agent, or Firm—James D. Christoff (57) ABSTRACT

An orthodontic force module is made of an elastomeric material and includes one or more eyelet segments along with one or more connector segments coupled to the eyelet segments. The configuration of the eyelet segments and the connector segments is arranged so that a substantially constant cross-sectional area is provided throughout the working length of the force module. As a result, the resistance to elongation is substantially uniform throughout the working range of the force module and premature degradation and failure due to relatively high, concentrated stresses are avoided.

34 Claims, 4 Drawing Sheets

ELASTOMERIC FORCE MODULE FOR ORTHODONTIC TREATMENT

BACKGROUND OF THE INVENTION

1. Field of the Invention

This invention relates to an elastomeric device that is used in the oral cavity during orthodontic treatment. More particularly, the present invention is directed to an elastomeric orthodontic force module that is useful for moving one or more teeth to desired locations along a dental arch, or for moving one dental arch relative to the other.

2. Description of the Related Art

Orthodontia is a specialized field within the general subject area of dentistry. Orthodontic treatment involves movement of malpositioned teeth to correct locations along the dental arch. In some instances, orthodontic treatment also includes movement of one dental arch as a unit relative to the other dental arch. Orthodontic treatment can result in improved occlusion as well as a more pleasing aesthetic appearance.

One type of orthodontic treatment involves the use of a set of components that are collectively known as "braces". In this type of treatment, small slotted devices known as brackets are secured to the patient's anterior, cuspid and bicuspid teeth. An archwire is received in the slots of the brackets and forms a track to guide movement of the teeth to desired positions.

Ends of orthodontic archwires are often received in enclosed passageways of small devices known as buccal tubes that are connected to the patient's molar teeth. The passageways of buccal tubes help prevent the ends of the archwire from contacting the patient's soft tissue in the oral cavity, which might otherwise lead to pain and injury. More importantly, buccal tubes often serve as points of connection for components that apply forces in the oral cavity, since the molar teeth associated with the buccal tubes have relatively large roots. These large roots provide relatively stable anchorage against the applied forces so that the other teeth connected to the force components are moved as a result.

A number of options are available during orthodontic treatment for applying forces to teeth in order to move the teeth to desired positions. Oftentimes, the practitioner will use the inherent resiliency of the archwire to apply a force to one or more brackets and move the associated teeth as the archwire tends to return to its normal relaxed configuration. If desired, one or more loops, bends, twists or other configurations may be formed in the archwire by the practitioner in order to help guide movement of the teeth as desired.

In some instances, orthodontic treatment may include correction of the alignment of the upper dental arch with the lower dental arch. For example, certain patients have a condition referred to as a Class II malocclusion wherein the lower dental arch is located an excessive distance in a rearward direction relative to the location of the upper dental arch when the jaws are closed. Other patients have an opposite condition referred to as a Class III malocclusion wherein the lower dental arch is located in a forward direction of its desired location relative to the position of the upper dental arch when the jaws are closed.

Orthodontic treatment of Class II and Class III malocclusions is commonly undertaken by movement of the upper dental arch as a single unit relative to movement of the lower dental arch as a single unit. To this end, forces are often applied to each dental arch as a unit by applying force to the brackets or buccal tubes, the archwires, or attachments that are connected to the brackets, buccal tubes or archwires. In this manner, a Class II or Class III malocclusion can be corrected at the same time that the archwires and brackets are used to move individual teeth along the dental arch to desired positions relative to each other.

Correction of Class II and Class III malocclusions is sometimes carried out by use of a force-applying system known as headgear. Headgear often includes strapping that extends around the rear of the patient's head. The strapping is often connected to tension springs that, in turn, are connected to the buccal tubes, the brackets, or one of the archwires. Additionally, and as an alternative for correction of Class III malocclusions, the strapping may be connected by tension springs to a chin cup that externally engages the patient's chin. In either instance, the strapping and springs serve to apply a rearwardly-directed force to the associated jaw.

However, headgear is often considered unsatisfactory because it is visibly apparent. Headgear may serve as a source of embarrassment, particularly among adolescent patients who may experience teasing from classmates. The embarrassment can be somewhat reduced if the orthodontist instructs the patient to wear the headgear only at night. Unfortunately, such practice may lengthen treatment time since the desired corrective forces are applied during only a portion of each calendar day.

Consequently, many practitioners and patients favor the use of intra-oral devices for correcting Class II and Class III malocclusions. Such devices are often located near the cuspid, bicuspid and molar teeth and away from the patient's anterior teeth. As a result, intra-oral devices for correcting Class II and Class III malocclusions are hidden in substantial part once installed and eliminate much of the patient embarrassment that is often associated with headgear.

A variety of force modules are known for treatment of Class II and Class III malocclusions. U.S. Pat. No. 6,120,289 describes a force module in the shape of a flat spring that assumes a curved orientation along its length when the patient's jaws are closed. During use, the inherent resiliency of the module tends to urge the module toward its normally straight configuration and as a result move the associated dental arches relative to each other.

Other types of force modules for correction of Class II and Class III malocclusions include telescoping assemblies that may optionally include a spring. An example of an improved telescoping force module is described in applicant's U.S. Pat. No. 5,964,588. In devices of this general type, the dental arches are moved relative to each other by the force of a coil spring or by a dead stop when the piston reaches the bottom of the cylinder, or by a combination of both.

Orthodontic force modules made of an elastomeric material have also been used in the past to treat Class II and Class III malocclusions. Elastomeric force modules are connected between the dental arches and often used in tension to pull the jaws together. The tension applied by the module tends to pull the jaws together in a direction along a reference line that extends between the points of attachment of the force module.

A variety of elastomeric orthodontic force modules are known. Examples of such force modules include bodies having the shape of a large O-ring and chain-type modules made of a number of smaller O-rings that are integrally connected together. Other types of elastomeric force modules include "dogbone-shaped" modules having a central, elongated straight section and a round eyelet section connected to each end of the straight central section.

While the elastomeric force modules described in the preceding paragraphs are generally considered satisfactory by many orthodontic practitioners, there is a continuing need in the art to improve the force modules that are currently available. For example, it would be desirable to provide an improved force module that is more resistant to fracture at a given tensile load without increasing the overall stiffness of the module. To this end, many attempts have been made to find alternative elastomeric materials that would be suitable for use in the oral cavity as force modules. To date, however, few orthodontic force modules with alternative materials are available.

SUMMARY OF THE INVENTION

The present invention is directed toward an improved orthodontic force module having a shape that provides more uniform stress along its length during use. As a result, premature degradation of the material and breakage that might otherwise be due to high, concentrated stresses in certain areas are avoided. The force module of the present invention may be elongated to a relatively large extent without rupturing.

The orthodontic force module of the present invention provides a number of important advantages. For one thing, a force module that is less likely to break during the course of treatment helps reduce the likelihood that the overall treatment time will be extended since the desired corrective forces are continuously provided without interruption. Additionally, the relatively low stresses encountered by the force module of the present invention during use helps to increase the length of time that the module may be used before replacement is needed. The principles of the present invention may be used for the construction of any orthodontic force module, regardless of the composition of the elastomeric material.

In more detail, the present invention in one embodiment is directed toward an orthodontic force module that is made of an elastomeric material and has a longitudinal axis. The force module comprises an eyelet segment having an opening, a first section and a second section. The first section and the second section extend along respective paths located on opposite sides of the opening. Each of the first section and the second section has a certain cross-sectional area in directions perpendicular to its respective path. The force module also includes a connector segment coupled to the eyelet segment and having a certain cross-sectional area in directions perpendicular to the longitudinal axis of the force module. The total area of the certain cross-sectional areas of the first section and the second section is in the range of about 80% to about 120% of the cross-sectional area of the connector segment when the force module is relaxed.

Another embodiment of the present invention is also directed to an orthodontic force module that is made of an elastomeric material and has a longitudinal axis. The force module of this embodiment comprises an eyelet segment having an opening with a longitudinal axis that extends in a direction generally parallel to the longitudinal axis of the force module when the force module is relaxed. The force module also includes a connector segment coupled to the eyelet segment.

An orthodontic force module according to another embodiment of the invention is also made of an elastomeric material and has a longitudinal axis. In this embodiment, the force module comprises an eyelet segment having an opening, a first section and a second section. The first section and the second section extend along opposite sides of the opening. Each of the first section and the second section includes a substantially straight first portion and a substantially straight second portion when the force module is relaxed. At least one first portion and at least one second portion have a longitudinal axis that extends at an acute angle relative to the longitudinal axis of the force module when the force module is relaxed. The force module also includes a connector segment coupled to the eyelet segment.

An additional embodiment of the present invention is also directed toward an orthodontic force module that is made of an elastomeric material and has a longitudinal axis. The force module of this embodiment comprises an eyelet segment having an opening, a first section and a second section. The first section and the second section extend along opposite sides of the opening and have respective central axes. The force module also includes a connector segment that is coupled to the eyelet segment and has a central axis. The connector segment, the first section and the second section elongate to approximately the same extent when considered in directions along their respective central axes when a tensile force is applied to the force module in directions along the longitudinal axis.

These and other aspects of the present invention are described in more detail below and are illustrated in the accompanying drawings.

DETAILED DESCRIPTION OF THE PREFERRED EMBODIMENTS

Figure 1:
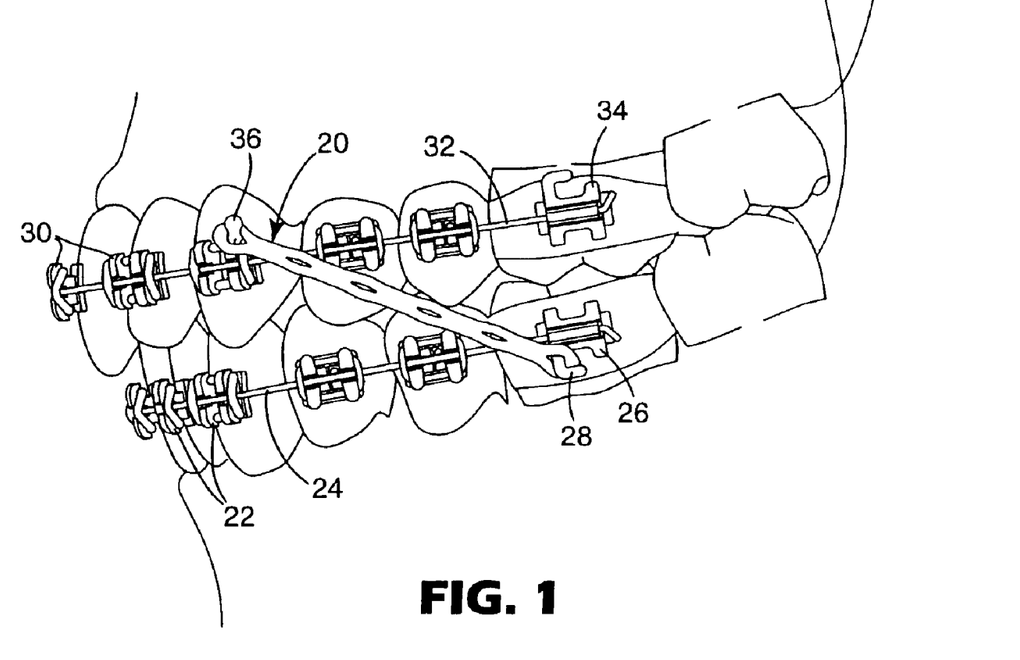
FIG. 1 is a schematic side elevational view of a patient undergoing orthodontic treatment, showing an exemplary force module of the present invention that is connected to the patient's upper and lower dental arches.

FIG. 1 is an illustration showing an exemplary use of an orthodontic force module 20 that is constructed according to one embodiment of the present invention. The force module 20 is installed in the oral cavity of an orthodontic patient undergoing treatment. The force module 20 in this example is arranged to correct a Class II malocclusion by urging the patient's lower dental arch in a forward direction relative to the patient's upper dental arch.

In more detail, a set of lower dental brackets 22 is secured to corresponding teeth of the patient's lower dental arch and an archwire 24 is placed in the slots of the brackets 22. Ends of the archwire 24 are received in buccal tubes 26 (only one shown) that are mounted on the patient's lower molar teeth. Each of the lower buccal tubes 26 has a hook 28 that extends in a distal direction (i.e., in a direction away from the middle of the patient's dental arch).

Similarly, a set of upper orthodontic brackets 30 is secured to teeth of the patient's upper dental arch and an archwire 32 is placed in the slots of the brackets 30. Ends of the archwire 32 are received in buccal tubes 34 (only one shown) that are mounted on the patient's upper molar teeth. In addition, one of the upper brackets 30 has a hook 36 that extends in a gingival direction (i.e., in a direction toward the patient's gingiva or gums).

The force module 20 is connected to the hook 28 as well as to the hook 36. The length of the force module 20 is selected by the practitioner so that the force module 20 is in tension when the patient's jaws are closed. This tensile force tends to urge the lower dental arch in a forward direction relative to the upper dental arch in order to correct the Class II malocclusion over a period of time.

Figure 2:
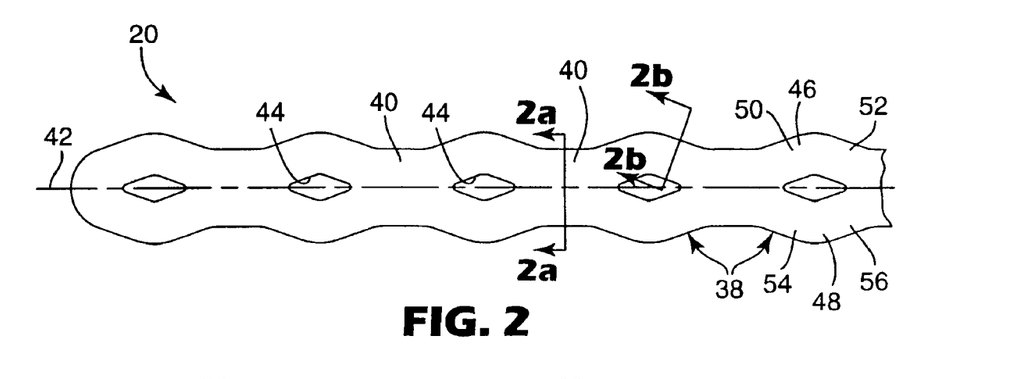
FIG. 2 is a fragmentary, enlarged side elevational view of the force module illustrated in FIG. 1 except that the force module is shown in its relaxed configuration.

The force module 20 is shown in more detail in FIG. 2. As illustrated, the force module 20 has a number of eyelet segments 38 that are integrally coupled together by connector segments 40. When the force module 20 is in its relaxed, normal configuration, the eyelet segments 38 and the connector segments 40 are all aligned along a straight path that coincides with a central longitudinal reference axis 42 of the force module 20.

Each of the eyelet segments 38 has a non-circular opening 44 that is in the general and overall shape of a parallelogram with four sides of equal length. Preferably, at least one and more preferably all of the interior corners of the parallelogram are rounded. Each of the openings 44 is elongated and has a longitudinal axis that coincides with the central references axis 42 of the force module 20. The openings 44 are sufficiently large to receive a hook or other component of an orthodontic system, such as the hooks 28, 36 depicted in FIG. 1. Preferably, the outermost eyelet segments 38 located on opposite ends of the force module 20 are connected to small extensions that serve to reinforce the adjacent openings 44 where high contact stress is likely to occur.

The eyelet segments 38 also include a first section 46 and a second section 48. The first section 46 and the second section 48 have respective central axes that extend along respective paths located along opposite sides of the corresponding opening 44. Each first section 46 includes a substantially straight first portion 50 and a substantially straight second portion 52 that is integrally connected to the first portion 50. Similarly, each of the second sections 48 includes a substantially straight first portion 54 and a substantially straight second portion 56 that is integrally connected to the first portion 54.

The force module 20 is illustrated in FIG. 2 in its normal, relaxed configuration. In this configuration, the longitudinal axes of the first portions 50, 54 and the longitudinal axes of the second portions 52, 56 all extend at an acute angle relative to the central longitudinal axis 42 of the force module 20. Optionally, all of such acute angles are approximately equal. An example of a suitable angle is 20 degrees, although other angles are also possible.

As a result, the longitudinal axis of the first portion 50 is oriented at an obtuse angle relative to the longitudinal axis of the second portion 52 when the force module 20 is relaxed. Likewise, the longitudinal axis of the first portion 54 is oriented at an obtuse angle relative to the longitudinal axis of the second portion 56 when the force module 20 is relaxed. Preferably, adjacent ends of the first and second portions 50, 52 are constructed to blend together to form a smooth curved configuration as shown in FIG. 2. A similar construction is provided for adjacent ends of the first and second portions 54, 56.

The connector segments 40 each have a central longitudinal axis that coincides with the central longitudinal axis of the force module 20. In addition, the sides of the connector segments 40 lie in reference planes that are parallel to the central axis 42. The connector segments 40 are of equal length in the embodiment shown in FIG. 2, although other constructions are also possible.

Figure 2A:
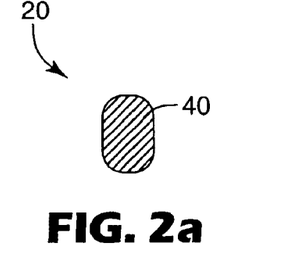
FIG. 2a is a cross-sectional view taken along lines 2a—2a of FIG. 2.
Figure 2B:
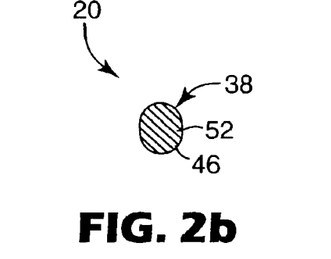
FIG. 2b is a cross-sectional view taken along lines 2b—2b of FIG. 2.

FIG. 2a is a cross-sectional view taken across one of the connector segments 40 in a reference plane that is perpendicular to the central axis 42. FIG. 2b is a cross-sectional view of one of the second portions 52, taken in a reference plane that is perpendicular to the central longitudinal axis of that portion. Cross-sectional views are not illustrated for the first portions 50, 54 or for the second portions 56, but preferably are all identical to the cross-sectional view shown for the second portion 52 in the illustrated embodiment.

Preferably, the cross-sectional area of the connector segment 40 as shown in FIG. 2 is within the range of about 80% to about 120% of the total of the cross-sectional areas of the first section 46 and the second section 48 of the eyelet segments 38. More preferably, the cross-sectional area of the connector segments 40 is within the range of about 90% to about 110% of the total of the cross-sectional areas of the first section 46 and the second section 48 of the eyelet segments 38. Most preferably, the cross-sectional area of the connector segment 40 is approximately equal to the total of the cross-sectional areas of the first and second sections 46, 48 and the cross-sectional areas of the first and the second sections 46, 48 are approximately equal as mentioned above.

Figure 3:
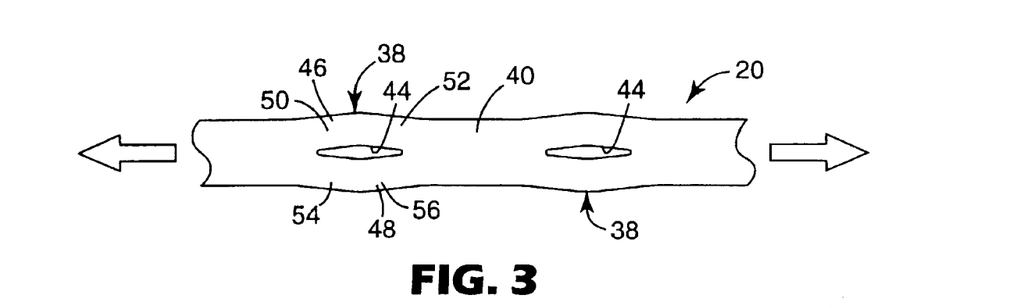
FIG. 3 is a view of a portion of the force module shown in FIG. 2 except that the force module has been elongated due to an applied tensile load.

FIG. 3 is an illustration of the force module 20 as it might appear when a tensile force is applied to its opposite ends in directions along the central axis 42 as represented by the arrows. As shown, the force module 20 elongates under tension. In particular, each of the eyelet segments 38 and each of the connector segments 40 elongate when a tensile force is applied to opposite ends of the force module 20.

Advantageously, the percent of elongation per unit length of the first and second sections 46, 48 in directions along their respective longitudinal axes is approximately equal to the percent of elongation per unit length of the connector segments 40 for a given applied tensile force. Such a relationship is possible because the total cross-sectional area of the first and second sections 46, 48 is substantially the same as the cross-sectional area of the connector segments 40. As a consequence, stresses are distributed uniformly throughout the force module 20 and relatively high localized stresses are unlikely to occur.

Moreover, and as can be appreciated by comparison of FIGS. 2 and 3, the overall configuration of the eyelet segments 38, including the angular orientation of the longitudinal axes of the portions 50, 56 does not substantially change when the force module 20 is stretched from its normal relaxed configuration shown in FIG. 2 to the elongated configuration shown in FIG. 3. Such construction helps to ensure that the stress is substantially the same regardless of whether the force module 20 is initially relaxed when tensile forces are applied, or whether the force module 20 is somewhat elongated when additional tensile forces are applied.

The force module 20 may be made of any elastomeric material that is suitable for use in the oral cavity and has sufficient strength to provide the forces needed for the orthodontic application at hand without rupture. Elastomeric materials include a natural or synthetic polymer which at room temperature can be repeatedly stretched to at least twice its original length and which after removal of the tensile stress, will quickly and forcibly return to approximately its original length. Suitable materials include durable, set-resistant thermoplastic urethane elastomers such as Texin brand urethane no. 285 from Bayer Corporation. Examples of suitable stain-resistant elastomers are set out in applicant's U.S. Pat. No. 5,461,133, which is incorporated by reference herein. The force module 20 is an integral, one-piece construction that can be made by, for example, an injection molding process, a compression molding process or by die cutting or stamping a section of previously molded material.

Figure 4:
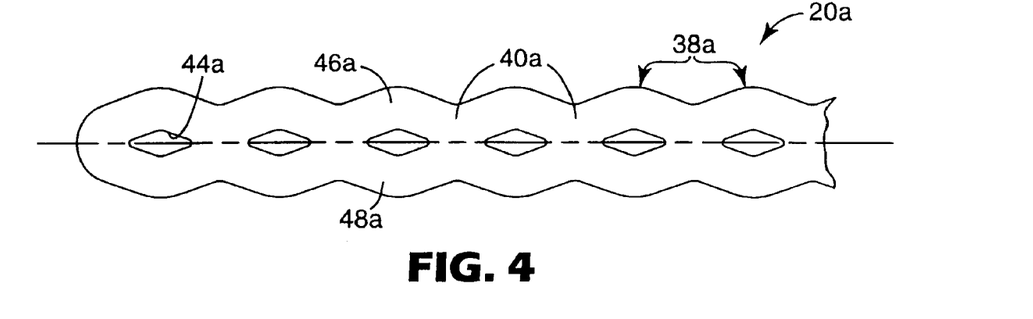
FIG. 4 is an enlarged, fragmentary side elevational view of an orthodontic force module according to another embodiment of the present invention.

A force module 20a according to another embodiment of the invention is illustrated in FIG. 4. The force module 20a includes a series of eyelet segments 38a and a series of connector segments 40a that are coupled to the eyelet segments 38a. Each of the eyelet segments 38a has an opening 44a along with a first section 46a and a second section 48a that extend along opposite sides of the opening 44a.

The connector segments 40a are substantially the same as the connector segments 40 described above, except that the connector segments 40a are somewhat shorter in directions along the longitudinal central axis of the force module 20a than the length of the connector segments 40 in the same direction. Optionally, the connector segments 40a may not be highly apparent to the eye. In that instance, the first section 46a and the second section 48a of one eyelet segment 38a may appear to be directly next to the first and second sections 46a, 48a respectively of the adjacent eyelet segment 38a. Other lengths may also be selected for the connector segments 40a as desired.

Other features of the force module 20a are essentially the same as the corresponding features of the force module 20. As such, a detailed description of the similar features need not be repeated.

Figure 5:
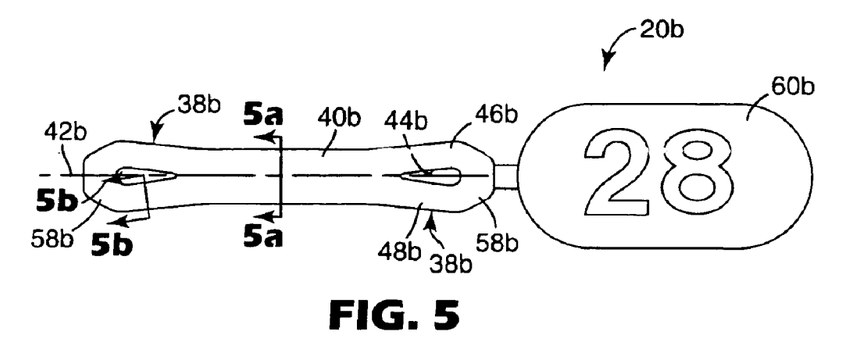
FIG. 5 is an enlarged side elevational view of an orthodontic force module according to still another embodiment of the present invention.

A force module 20b according to another embodiment of the invention is illustrated in FIG. 5. The force module 20b has only two eyelet segments 38b and a single connector segment 40b that interconnects the eyelet segments 38b.

Each of the eyelet segments 38b includes a first section 46b and a second section 48b that extend along opposite sides of an opening 44b. Additionally, an end section 58b interconnects the first and second sections 46b, 48b. The opening 44b has a longitudinal axis that coincides with the central longitudinal axis 42b of the force module 20b.

Figure 5A:
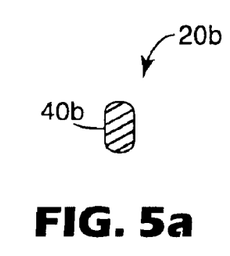
FIG. 5a is a cross-sectional view of the orthodontic force module shown in FIG. 5 and taken along lines 5a—5a of FIG. 5.
Figure 5B:
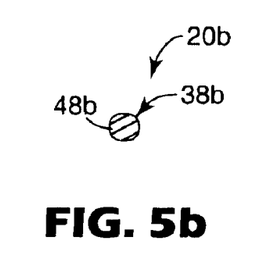
FIG. 5b is a cross-sectional view of the orthodontic force module shown in FIG. 5 and taken along lines 5b—5b of FIG. 5.

FIG. 5a is a cross-sectional view taken in a reference plane perpendicular to the central axis 42b of the connector segment 40b, looking along lines 5a—5a of FIG. 5. FIG. 5b is a cross-sectional view looking in a direction along a central longitudinal axis of the second section 48b and taken along lines 5b—5b of FIG. 5. A similar cross-sectional view taken across the first section 46b is not illustrated but is identical to the cross-section shown in FIG. 5b.

The total area of the cross-sectional areas of the sections 46b, 48b taken in reference planes perpendicular their respective longitudinal axes is approximately equal to the cross-sectional area of the connector segment 40b taken in a reference plane perpendicular to the central longitudinal axis of the force module 20. Such relationship can be appreciated by comparing FIG. 5a to FIG. 5b, since the cross-sectional area of FIG. 5a is approximately twice the cross-sectional area of FIG. 5b.

Optionally, the cross-sectional area of the end sections 58b is larger than the cross-sectional area of the second section 48b shown in FIG. 5b. Such construction serves to reinforce the end section 58b to help resist fracture when the force module 20b in connected to hooks, posts or other orthodontic components. Reinforced end sections similar to the end sections 58b also may be used on the outermost eyelet segments of the force modules 20, 20a if desired.

As an additional option, and as illustrated in FIG. 5, the force module 20b includes a tab 60b that is integrally connected to one of the end sections 58b by a molding gate. The tab 60b is useful as a handle during installation for the force module 20b. As an example, the opening 44b of the free end of the force module 20b may be connected to an orthodontic component, and the tab 60b may then be used by the practitioner to stretch the force module 20b and guide the opening 44b on the opposite end of the force module 20b over a second orthodontic component. The tab 60b and the associated gate are then cut away from the remaining portions of the force module 20b and discarded.

Advantageously, the tab 60b also serves as a location for display of information or identification markings. For example, and as depicted in FIG. 5, the tab 60b may bear the number "28" to indicate the installed length or working length of the force module 20b in millimeters when the force module 20b is in place. Preferably, the indicated length represents a length between the center of the openings 44b.

Furthermore, the tab 60b may provide an overflow reservoir during an injection molding process. Provision of the reservoir assures that a solid knit in the material may be achieved when the adjacent eyelet segment 38b is formed. Although not shown in the drawings, the elastomeric material in such an injection molding process is introduced into the mold cavity through a gate that is located on the opposite end of the force module 20b, preferably next to the end section 58b and in alignment with the central axis 42b.

Optionally, a number of force modules 20b of varying lengths are provided in pairs on a single sprue for convenient storage, handling and delivery to the operatory. Other features of the force module 20b are preferably the same as the corresponding features described in connection with the force module 20.

Figure 6:
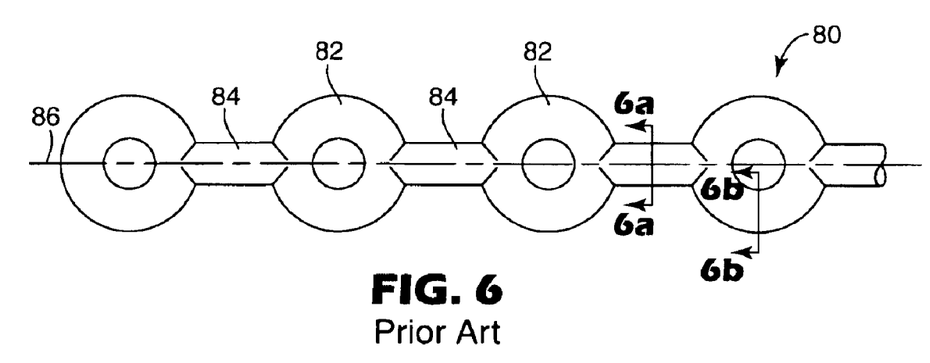
FIG. 6 is an enlarged fragmentary side elevational view of an exemplary prior art orthodontic force module.

FIG. 6 is an illustration of an exemplary prior art force module 80 that is made by an injection-molding process. The force module 80 includes a number of circular eyelet segments 82 and a number of straight connector segments 84 that are coupled between adjacent pairs of eyelet segments 82. The eyelet segments 82 and the connector segments 84 are arranged in series along a central longitudinal axis 86.

Figure 6A:
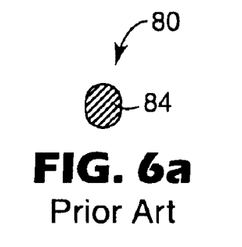
FIGS. 6a and 6b are cross-sectional views taken along lines 6a—6a and 6b—6b respectively.
Figure 6B:
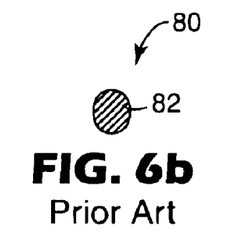

FIG. 6a is a cross-sectional view of a connector segment 84, taken along lines 6a—6a of FIG. 6 and in directions parallel to the central axis 86. FIG. 6b is taken along lines 6b—6b of FIG. 6 and is a cross-sectional view of one of the eyelet segments 82. The cross-section of the eyelet segment 82 represented in FIG. 6b is substantially the same along the entire circular length of the eyelet segments 82, and is essentially identical to the cross-section of the connector segment 84 as shown in FIG. 6a.

Figure 7:
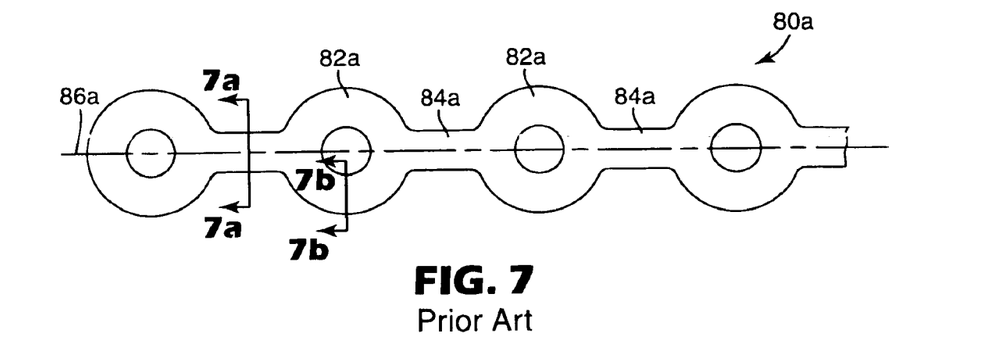
FIG. 7 is an enlarged fragmentary side elevational view of another prior art orthodontic force module.

FIG. 7 is an illustration of another orthodontic force module 80a according to the prior art. The force module 80a is made by a die-stamping process, in contrast to the injection molding process used to make the force module 80. The force module 80a includes a series of circular eyelet segments 82a that are interconnected by connector segments 84a. The cross-sectional views of FIGS. 7a and 7b, taken along lines 7a—7a and lines 7b—7b of FIG. 7 respectively, illustrate the essentially identical cross-sectional configurations of the connector segments 84a and the eyelet segments 82a respectively.

Figure 8:
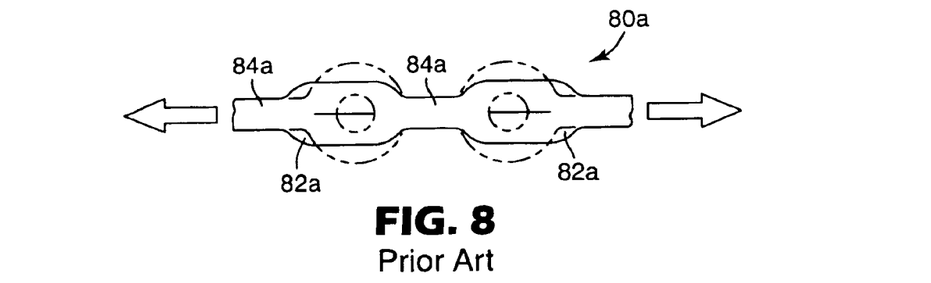
FIG. 8 is an enlarged fragmentary side elevational view of a portion of the prior art orthodontic force module shown in FIG. 7, depicting the force module as it appears when a relatively low tensile force is applied.

FIG. 8 is a fragmentary, somewhat schematic view showing a portion of the force module 80a as it appears when a tensile force is applied in opposite directions along the central axis 86a as indicated by the arrows. The dashed lines in FIG. 8 represent the overall appearance of the same force module 80a when relaxed. As illustrated, the eyelet segments 82a shift from a circular configuration to a straightened configuration with parallel sections on opposite sides of the now-closed eyelet opening when tension is applied.

Figure 7A:
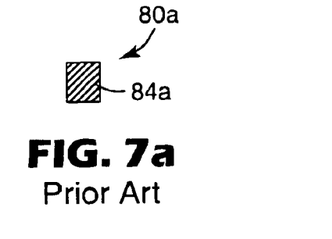
FIGS. 7a and 7b are cross-sectional views taken along lines 7a—7a and 7b—7b respectively.
Figure 7B:
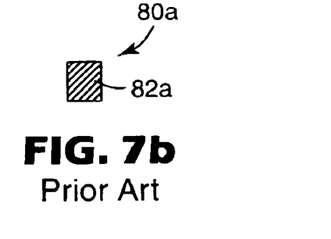
Figure 9:
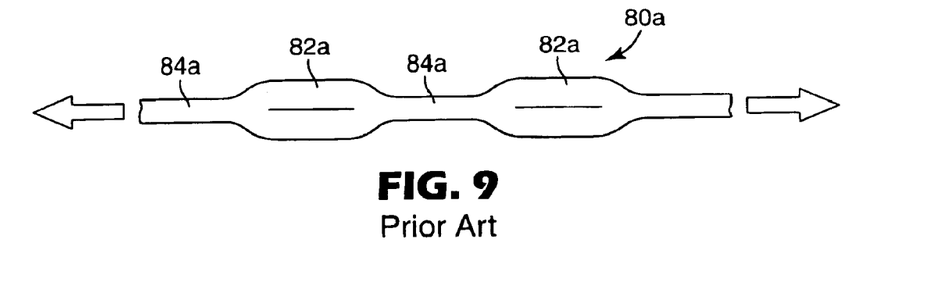
FIG. 9 is a view somewhat similar to FIG. 8 except that the force module is depicted as it appears when a somewhat higher tensile force is applied.

FIG. 9 is an illustration similar to FIG. 8, except that the tensile force applied to the force module 80a is greater in FIG. 9 than the tensile force applied to the force module 80a in FIG. 8. As shown in FIG. 9, the increased tensile force tends to elongate the entire force module 80a, but greater elongation is observed in regions of the connector segments 84a in comparison to the elongation of the eyelet segments 82a. This characteristic of non-uniform elongation is due at least in part to the fact that the cross-sectional area across the two sections of the eyelet segment 82a is twice as large as the cross-sectional area of the connector segment 84a, as depicted by FIGS. 7a and 7b and indicated above. As a consequence, the connector segments 84a tend to elongate more than the eyelet segments 82a when a tensile force is applied.

Moreover, and referring again to FIG. 8, the initial elongation of the force module 80a occurs when the eyelet segments 82a are collapsed. The force required to collapse the eyelet segments 82a is typically smaller than the force required to elongate the connector segments 84a to any appreciable extent. As a result, the force module 80a provides resistance to elongation at two different force levels: first, the force required to collapse the eyelet segments 82a, and second, the force required to elongate the connector segments 84a as shown in FIG. 9 once the eyelet segments 82a have been collapsed. Such a characteristic may not be satisfactory in some orthodontic applications where a substantially uniform resistance to elongation is desired regardless of the preexisting amount of elongation.

The force modules 20, 20a, 20b as described above can be used in a variety of applications. Exemplary uses include applications for Class II correction as shown for example in FIG. 1 as well as applications for correction of Class III malocclusion. However, other uses are also possible. For example, the force modules of the invention can be used to close spaces that are present along one or more dental arches, such as may occur when a tooth is removed. To close spaces, the force modules may be connected between hooks, posts or other structures that are provided on brackets, on buccal tubes or on locations along a single archwire. The force modules may also be used for consolidation of a dental arch, wherein each bracket of a series of brackets along a single dental arch extends through a corresponding opening.

Those skilled in the art may recognize that a number of variations and additions are possible to the presently preferred embodiments described above and illustrated in the drawings. Accordingly, the present invention should not be deemed limited to the specific embodiments described in detail, but instead only by a fair scope of the claims that follow along with their equivalents.

What is claimed is:

1. An orthodontic force module made of an elastomeric material and having a longitudinal axis, the force module comprising:

an eyelet segment having an opening, a first section and a second section, wherein the first section and the second section extend along respective paths located on opposite sides of the opening, each of the first section and the second section having a certain cross-sectional area in directions perpendicular to its respective path; and a connector segment coupled to the eyelet segment and having a certain cross-sectional area in directions perpendicular to the longitudinal axis of the force module, wherein the total area of the certain cross-sectional areas of the first section and the second section is in the range of about 80% to about 120% of the cross-sectional area of the connector segment when the force module is relaxed, wherein the opening has a generally parallelogram-shaped configuration, and wherein the opening has at least one rounded interior corner.

2. An orthodontic force module made of an elastomeric material and having a longitudinal axis, the force module comprising:

an eyelet segment having an opening, a first section and a second section, wherein the first section and the second section extend along respective paths located on opposite sides of the opening, each of the first section and the second section having a certain cross-sectional area in directions perpendicular to its respective path;

a connector segment coupled to the eyelet segment and having a certain cross-sectional area in directions perpendicular to the longitudinal axis of the force module, wherein the total area of the certain cross-sectional areas of the first section and the second section is in the range of about 80% to about 120% of the cross-sectional area of the connector segment when the force module is relaxed; and a tab connected to the eyelet segment, wherein the tab includes indicia representative of the length of the force module.

3. An orthodontic force module according to claim 2 wherein the indicia that is representative of length of the force module is an indicia that represents the working length of the force module.

4. An orthodontic force module made of an elastomeric material and having a longitudinal axis, the force module comprising:

an eyelet segment having an opening, a first section and a second section, wherein the first section and the second section extend along respective paths located on opposite sides of the opening, each of the first section and the second section having a certain cross-sectional area in directions perpendicular to its respective path; and a connector segment coupled to the eyelet segment and having a certain cross-sectional area in directions perpendicular to the longitudinal axis of the force module, wherein the total area of the certain cross-sectional areas of the first section and the second section is in the range of about 80% to about 120% of the cross-sectional area of the connector segment when the force module is relaxed, wherein the opening is elongated and has a longitudinal axis that extends in a direction generally parallel to the longitudinal axis of the force module when the force module is relaxed.

5. An orthodontic force module according to claim 4 wherein at least one of the first section and the second section includes a substantially straight first portion and a substantially straight second portion when the force module is relaxed, wherein at least one first portion and at least one second portion have a longitudinal axis that extends at an acute angle relative to the longitudinal axis of the force module when the force module is relaxed.

6. An orthodontic force module made of an elastomeric material and having a longitudinal axis, the force module comprising:

an eyelet segment having an opening, a first section and a second section, wherein the first section and the second section extend along respective paths located on opposite side of the opening, each of the first section and the second section having a certain cross-sectional area in directions perpendicular to its respective path; and a connector segment coupled to the eyelet segment and having a certain cross-sectional area in directions perpendicular to the longitudinal axis of the force module, wherein the total area of the certain cross-sectional areas of the first section and the second section is in the range of about 80% to about 120% of the cross-sectional area of the connector segment when the force module is relaxed, wherein the connector segment, the first section and the second section have respective central axes, and wherein the connector segment, the first section and the second section elongate to approximately the same extent when considered in directions along their respective central axes when a tensile force is applied to the force module in directions along the longitudinal axis.

7. An orthodontic force module according to claim 6, wherein the total area of the certain cross-sectional areas of the first section and the second section is in the range of about 90% to about 110% of the cross-sectional area of the connector segment when the force module is relaxed.

8. An orthodontic force module according to claim 6 wherein the total area of the certain cross-sectional areas of the first section and the second section is approximately equal to the cross-sectional area of the connector segment when the force module is relaxed.

9. An orthodontic force module according to claim 6 wherein the force module includes at least one additional eyelet segment.

10. An orthodontic force module according to claim 9 wherein the force module includes at least one additional connector segment that is coupled to at least one of the eyelet segments.

11. An orthodontic force module according to claim 6 wherein the first section and the second section each include a first portion and a second portion coupled to the first portion, and wherein the first portion and the second portion of at least one section have respective longitudinal axes that each extend at an acute angle relative to the longitudinal axis of the force module when the force module is relaxed.

12. An orthodontic force module according to claim 11 wherein the first portion and the second portion of at least one section have respective straight longitudinal axes that are oriented at an obtuse angle relative to each other when the force module is relaxed.

13. An orthodontic force module made of an elastomeric material and having a longitudinal axis, the force module comprising:

an eyelet segment having an opening with a longitudinal axis that extends in a direction generally parallel to the longitudinal axis of the force module when the force module is relaxed; and a connector segment coupled to the eyelet segment, wherein the force module includes at least one additional eyelet segment, and wherein the force module includes at least one additional connector segment that is coupled to at least one of the eyelet segments.

14. An orthodontic force module according to claim 13 wherein the longitudinal axis of the opening coincides with the longitudinal axis of the force module.

15. An orthodontic force module according to claim 13 wherein the eyelet segment includes a first section and the second section each having a first portion and the second portion coupled to the first portion, and wherein the first portion and the second portion of at least one section have respective longitudinal axes that extend at an acute angle relative to the longitudinal axis of the force module when the force module is relaxed.

16. An orthodontic force module according to claim 15 wherein the first portion and the second portion of at least one section have respective straight longitudinal axes that are oriented at an obtuse angle relative to each other when the force module is relaxed.

17. An orthodontic force module according to claim 13 wherein the opening has a generally parallelogram-shaped configuration.

18. An orthodontic force module according to claim 17 wherein the opening has at least one rounded interior corner.

19. An orthodontic force module according to claim 13 and including a tab connected to the eyelet segment.

20. An orthodontic force module made of an elastomeric material and having a longitudinal axis, the force module comprising:

an eyelet segment having an opening with a longitudinal axis that extends in a direction generally parallel to the longitudinal axis of the force module when the force module is relaxed; and a connector segment coupled to the eyelet segment, wherein the eyelet segment includes a first section and a second section having respective central axes, wherein the connector segment has a central axis, and wherein the connector segment, the first section and the second section elongate to approximately the same extent when considered in directions along their respective central axes when a tensile force is applied to the force module in directions along the longitudinal axis.

21. An orthodontic force module made of an elastomeric material and having a longitudinal axis, the force module comprising:

an eyelet segment having an opening, a first section and a second section, wherein the first section and the second section extend along opposite sides of the opening, wherein each of the first section and the second section includes a substantially straight first portion and a substantially straight second portion when the force module is relaxed, wherein at least one first portion and at least one second portion have a longitudinal axis that extends at an acute angle relative to the longitudinal axis of the force module when the force module is relaxed; and a connector segment coupled to the eyelet segment.

22. An orthodontic force module according to claim 21 wherein the force module includes at least one additional eyelet segment.

23. An orthodontic force module according to claim 22 wherein the force module includes at least one additional connector segment that is coupled to at least one of the eyelet segments.

24. An orthodontic force module according to claim 21 wherein the opening has a generally parallelogram-shaped configuration.

25. An orthodontic force module according to claim 24 wherein the opening has at least one rounded interior corner.

26. An orthodontic force module according to claim 21 and including a tab connected to the eyelet segment.

27. An orthodontic force module according to claim 26 wherein the tab includes indicia that is representative of the working length of the force module.

28. An orthodontic force module according to claim 21 wherein the connector segment, the first section and the central section each have a respective central axis, and wherein the connector segment, the first section and the second section elongate to approximately the same extent when considered in directions along their respective central axes when a tensile force is applied to the force module in directions along the longitudinal axis.

29. An orthodontic force module made of an elastomeric material and having a longitudinal axis, the force module comprising:

an eyelet segment having an opening, a first section and a second section, wherein the first section and the second section extend along opposite sides of the opening and have respective central axes;

a connector segment coupled to the eyelet segment and having a central axis, wherein the connector segment, the first section and the second section elongate to approximately the same extent when considered in directions along their respective central axes when a tensile force is applied to the force module in directions along the longitudinal axis of the force module, wherein the opening has a generally parallelogram-shaped configuration.

30. An orthodontic force module according to claim 29 wherein the force module includes at least one additional eyelet segment.

31. An orthodontic force module according to claim 30 wherein the force module includes at least one additional connector segment that is coupled to at least one of the eyelet segments.

32. An orthodontic force module according to claim 29 wherein the opening has at least one rounded interior corner.

33. An orthodontic force module made of an elastomeric material and having a longitudinal axis, the force module comprising:

an eyelet segment having an opening, a first section and a second section, wherein the first section and the second section extend along opposite sides of the opening and have respective central axes;

a connector segment coupled to the eyelet segment and having a central axis, wherein the connector segment, the first section and the second section elongate to approximately the same extent when considered in directions along their respective central axes when a tensile force is applied to the force module in directions along the longitudinal axis of the force module; and a tab connected to the eyelet segment.

34. An orthodontic force module according to claim 33 wherein the tab includes indicia that is representative of the length of the force module.

\* \* \* \* \*

UNITED STATES PATENT AND TRADEMARK OFFICE
CERTIFICATE OF CORRECTION

PATENT NO. : 6,935,858 B2
DATED : August 30, 2005
INVENTOR(S) : Cleary, James D.

It is certified that error appears in the above-identified patent and that said Letters Patent is hereby corrected as shown below:

Column 11,
Line 30, delete "side" and insert -- sides --, therefor.

Signed and Sealed this

Twenty-fifth Day of October, 2005

JON W. DUDAS
*Director of the United States Patent and Trademark Office*